(12) United States Patent
Garel

(10) Patent No.: US 8,791,308 B2
(45) Date of Patent: Jul. 29, 2014

(54) PROCESS FOR THE HYDROXYLATION OF PHENOLS AND OF PHENOL ETHERS

(75) Inventor: Laurent Garel, Lyons (FR)

(73) Assignee: Rhodia Operations, Aubervilliers (FR)

( * ) Notice: Subject to any disclaimer, the term of this patent is extended or adjusted under 35 U.S.C. 154(b) by 299 days.

(21) Appl. No.: 13/259,860

(22) PCT Filed: Mar. 30, 2010

(86) PCT No.: PCT/EP2010/054232
§ 371 (c)(1),
(2), (4) Date: Oct. 12, 2011

(87) PCT Pub. No.: WO2010/115784
PCT Pub. Date: Oct. 14, 2010

(65) Prior Publication Data
US 2012/0035397 A1    Feb. 9, 2012

(30) Foreign Application Priority Data

Apr. 6, 2009   (FR) ...................................... 09 01660

(51) Int. Cl.
*C07C 37/08*   (2006.01)
(52) U.S. Cl.
USPC ............................ 568/768; 568/629; 568/771
(58) Field of Classification Search
None
See application file for complete search history.

(56) References Cited

U.S. PATENT DOCUMENTS

| 3,849,502 | A | * | 11/1974 | Bourdin et al. | ............... 568/629 |
| 4,223,165 | A | * | 9/1980 | Jouffret | ........................ 568/771 |
| 4,301,307 | A | | 11/1981 | Jouffret | |
| 5,245,086 | A | * | 9/1993 | Costantini et al. | ............ 568/629 |

FOREIGN PATENT DOCUMENTS

| EP | 0 480 800 A1 | 4/1992 |
| FR | 2.071.464 A | 9/1971 |
| FR | 2 266 683 A1 | 10/1975 |
| FR | 2 318 851 A1 | 2/1977 |
| FR | 2 655 332 A1 | 6/1991 |
| GB | 1 448 358 | 9/1976 |

OTHER PUBLICATIONS

International Search Report (PCT/ISA/210) issued on May 4, 2010, by European Patent Office as the International Searching Authority for International Application No. PCT/EP2010/054232.

* cited by examiner

*Primary Examiner* — Sudhakar Katakam
(74) *Attorney, Agent, or Firm* — Dentons US LLP

(57) ABSTRACT

A process for the hydroxylation of phenols and of phenol ethers by hydrogen peroxide is described. More particularly a process for the hydroxylation of phenol by hydrogen peroxide is described. The described process can include hydroxylation of a phenol or of a phenol ether having at least one hydrogen atom at the ortho and para position of the hydroxyl group or of the ether group, by reaction of said phenol or phenol ether, with hydrogen peroxide, in the presence of an acid catalyst, wherein the reaction is carried out in the presence of an effective amount of a catalyst which is a mixture of at least two strong acids and wherein one of the acids is chosen from strong protonic acids and the other acid is chosen from superacids.

33 Claims, No Drawings

PROCESS FOR THE HYDROXYLATION OF PHENOLS AND OF PHENOL ETHERS

This application is the United States national phase of PCT/EP2010/054232, filed Mar. 30, 2010, and designating the United States (published in the French language on Oct. 14, 2010, as WO 2010/115784 A1; the title and abstract were also published in English), which claims foreign priority under 35 U.S.C. §119 of FR 0901660, filed Apr. 6, 2009, each hereby expressly incorporated by reference in its entirety and each assigned to the assignee hereof.

The subject of the present invention is a process for the hydroxylation of phenols and of phenol ethers by hydrogen peroxide.

The invention more particularly targets a process for the hydroxylation of phenol by hydrogen peroxide.

The phenol hydroxylation reaction is not selective and two isomers are obtained, namely 1,4-dihydroxybenzene or hydroquinone (HQ) and 1,2-dihydroxybenzene or pyrocatechol (PC).

The proportion of the two diphenols may vary quite widely and depends on the process used.

The production of diphenols on an industrial scale requires plants dedicated to a given process which may predominantly result either in hydroquinone or in pyrocatechol.

Currently, since the market has a greater demand for pyrocatechol, a process for the hydroxylation of phenol is therefore sought which predominantly results in pyrocatechol.

It therefore turns out that in order to meet the demand of the market, it is important to provide an industrial process that makes it possible to increase the production of pyrocatechol formed relative to the amount of hydroquinone.

Many processes for the hydroxylation of phenols are described in the prior art.

Mention is made, inter alia, of patent FR-A 2 071 464 which relates to a very important industrial process for the hydroxylation of phenols and of phenol ethers that makes it possible to attain, in particular, hydroquinone and pyrocatechol during the application of this process to phenol.

Said process consists in carrying out the hydroxylation, by hydrogen peroxide, in the presence of a strong acid. Among these strong acids, sulfuric acid, p-toluenesulfonic acid, and perchloric acid are the most commonly used.

Although this process is very advantageous, it has the drawback of requiring, at low temperature, the use of a large amount of catalyst ranging up to 20% of the weight of hydrogen peroxide used. In the case of a smaller amount being used, a longer reaction time is required, for example 10 hours.

The hydroxylation of phenol is described in FR-A 2 318851, in trifluoromethanesulfonic acid and in FR-A 2 655 332, in the presence of an effective amount of at least one alkali or alkaline-earth metal salt of at least one protonic acid having a pKa in water of less than −0.1 and of an effective amount of the free protonic acid.

In the aforementioned three patents, the use of an oxyacid of phosphorus such as for example phosphoric acid is described.

The latter is not cited as a strong protonic acid but as an agent for complexing metal ions (Fe, Cu, Cr, Co, Mn, V) which are introduced by the reactants and which have the distinctive feature of degrading the reaction yield of hydroxylation products.

Furthermore, a process is known according to FR-A 2 266 683 which consists in carrying out the hydroxylation of phenol, in the presence of a ketone.

It results in an improvement in the hydroquinone and pyrocatechol yield of the reaction. All the examples described result in a larger amount of pyrocatechol than that of hydroquinone and the PC/HQ ratio varies only between 1 and 1.72.

In EP-A 0 480 800, a process was proposed on the contrary that makes it possible to increase the amount of hydroquinone formed relative to the amount of pyrocatechol, by using an aromatic type ketone.

In accordance with the process described in EP-A 0 480 800, the presence of this type of ketone during the hydroxylation of phenol acts on the regioselectivity of the reaction, and PC/HQ ratios that vary between 0.9 and 1.1 are advantageously obtained.

One of the objectives of the invention is to provide a phenol hydroxylation process that makes it possible to increase the amount of pyrocatechol formed relative to the amount of hydroquinone.

Another objective of the invention is to provide a phenol hydroxylation process that makes it possible to obtain more pyrocatechol while retaining high yields of diphenols.

Furthermore, the problem is that over time the demand of the market fluctuates and requires variable amounts of pyrocatechol and of hydroquinone.

It is difficult to adapt the diphenol production of the industrial units to the demand of the market.

Another objective of the invention is therefore to provide a flexible process that makes it possible to thus adjust the pyrocatechol/hydroquinone ratio and thus to easily adapt production to the demand of the market.

More particularly, the subject of the present invention is a process for the hydroxylation of a phenol or of a phenol ether having at least one hydrogen atom at the ortho and the para position of the hydroxyl or ether group, by reaction of said phenol or phenol ether, with hydrogen peroxide, in the presence of an acid catalyst, characterized in that the reaction is carried out in the presence of an effective amount of a catalyst which is a mixture of at least two strong acids and which is characterized in that a mixture of at least two acids is used:

one of the acids being selected from strong protonic acids having a $pK_a$ (S) greater than or equal to that of sulfuric acid and a $\Delta pK_a$ (S) with respect to sulfuric acid less than or equal to 4 and greater than or equal to 0, and the other acid being selected from superacids.

In the present account of the invention, the expression "strong protonic acid" denotes an acid having a $pK_a$ (S) greater than or equal to that of sulfuric acid: (S) representing the organic solvent which is nitrobenzene.

The term "superacid" is understood to mean an acid having a $pK_a$ (S) below that of sulfuric acid.

The $pK_a$ (S) is defined as the ionic dissociation constant of the acid/base pair in a solvent (S).

The $pK_a$ of the acids suitable for the process of the invention is defined with reference to a potentiometry measurement carried out in a solvent which is nitrobenzene (S) and the measurement protocol of which is explained before the examples.

The acids that are involved in the process of the invention are defined later on, by a difference in $pK_a$, $\Delta pK_a$, which corresponds, for one and the same solvent, to the difference between the $pK_a$ of the chosen acid and the $pK_a$ of sulfuric acid.

It has unexpectedly been observed that the use, during the hydroxylation of phenol by hydrogen peroxide, of a mixture of acids having a different acidity, exerts an action on the regioselectivity of the reaction and makes it possible, depending on the choice of the acids, to increase the formation of pyrocatechol, by increasing the production of this compound relative to hydroquinone.

It has also been found that it was possible to adjust the pyrocatechol/hydroquinone ratio obtained by varying the relative proportions of the various acids of the mixture.

It should be noted that the oxyacids of phosphorus described in the literature that are defined as being acid-functional compounds of phosphorus in the +5 oxidation state are not considered to be strong protonic acids within the meaning of the invention. A comparative example provided in the experimental section demonstrates that a phosphoric acid cannot be considered to be equivalent to sulfuric acid or another strong protonic acid of the invention.

According to one variant of the process of the invention, the oxyacids of phosphorus may be used in the process of the invention to fulfill their role of complexing agents, in addition to the mixture of acids recommended by the invention.

The process of the invention applies both to phenols and to phenol ethers which are denoted in the present text by the term "substrate".

The process of the invention is well suited to the hydroxylation of phenol but also to substituted phenolic compounds.

The expression "substituted phenolic compounds" is understood to mean an aromatic compound, in which one of the hydrogen atoms of the aromatic ring is replaced by a hydroxyl group and at least one other hydrogen atom is replaced by a substituent.

The nature of the substituent(s) is irrelevant as long as they do not disrupt the production of the desired product.

The present invention applies very particularly to the substrates of general formula (I):

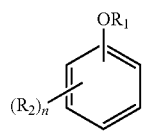

(I)

in said formula:
  n is a number from 0 to 4, preferably equal to 0, 1 or 2;
  $R_1$ represents a hydrogen atom, or an alkyl, cycloalkyl, aryl or aralkyl group; and
  $R_2$, which are identical or different, represent an alkyl group, an alkoxy group, a hydroxyl group, a halogen atom, a haloalkyl or perhaloalkyl group.

In the formula (I), the $OR_1$ group is an ether group when $R_1$ is other than a hydrogen atom.

Within the context of the invention, the term "alkyl" is understood to mean a $C_1$-$C_{15}$, preferably $C_1$-$C_{10}$ and more preferably still $C_1$-$C_4$, linear or branched hydrocarbon-based chain. Examples of preferred alkyl groups are in particular methyl, ethyl, propyl, isopropyl, butyl, isobutyl and t-butyl.

The term "alkoxy" is understood to mean an alkyl-O-group in which the term alkyl has the meaning given above. Preferred examples of alkoxy groups are methoxy or ethoxy groups.

The term "cycloalkyl" is understood to mean a $C_3$-$C_8$ monocyclic, cyclic hydrocarbon-based group, preferably a cyclopentyl or cyclohexyl group or a $C_4$-$C_{18}$ polycyclic (bicyclic or tricyclic), cyclic hydrocarbon-based group, in particular adamantyl or norbornyl.

The term "aryl" is understood to mean an aromatic monocyclic or polycyclic group, preferably a $C_6$-$C_{20}$ monocyclic or bicyclic group, preferably phenyl or naphthyl. When the group is polycyclic, that is to say that it comprises more than one cyclic ring, the cyclic rings may be fused together in pairs or attached together in pairs by σ bonds. Examples of ($C_6$-$C_{18}$)aryl groups are in particular phenyl and naphthyl.

The term "aralkyl" is understood to mean a linear or branched hydrocarbon-based group bearing a $C_7$-$C_{12}$ monocyclic aromatic ring, preferably benzyl: the aliphatic chain comprising one or two carbon atoms.

The expression "haloalkyl group" is understood to mean an alkyl group as defined previously, in which one or more hydrogen atoms are replaced by a halogen atom, preferably a fluorine atom.

The expression "perhaloalkyl group" is understood to mean an alkyl group comprising from 1 to 10 carbon atoms and from 3 to 21 halogen atoms, preferably fluorine atoms and more particularly the trifluoromethyl group.

The expression "halogen atom" defines fluorine, chlorine and bromine.

The process of the invention preferably applies to the substrates corresponding to the formula (I) in which n is equal to 0 or 1; $R_1$ represents a hydrogen atom, or an alkyl group having from 1 to 4 carbon atoms; $R_2$ represents a hydrogen atom, or an alkyl or alkoxy group having from 1 to 4 carbon atoms.

The substrates to which the process of the invention applies are in particular phenol; aliphatic ethers of phenols; monoalkylphenols, dialkylphenols, trialkylphenols with $C_1$-$C_4$ alkyl groups; and alkoxyphenols with $C_1$-$C_4$ alkoxy groups.

Among the substrates of formula (I) which could be used in the process of the invention, mention may be made, nonlimitingly, of phenol; aliphatic ethers of phenol such as anisole, phenetole; alkylphenols such as o-cresol, m-cresol; alkoxyphenols such as 2-methoxyphenol (guaiacol), and 2-ethoxyphenol (guaethol).

The present process is very particularly suitable for the preparation of hydroquinone and pyrocatechol from phenol.

In accordance with the process of the invention, the choice of the use of a mixture of acids and the choice of the acids used in said mixture act on the regioselectivity of the reaction.

The feature of the process of the invention is to use, as reaction catalyst, a mixture of at least two acids which have a different acidity.

As mentioned previously, the strong protonic acid is an acid having a $pK_a$ (S) greater than or equal to that of sulfuric acid.

The strong protonic acids used in the process of the invention have a $\Delta pK_a$ (S) with respect to sulfuric acid less than or equal to 4 and greater than or equal to 0.

More preferably still, the strong protonic acids have a $\Delta pK_a$ (S) with respect to sulfuric acid less than or equal to 3 and greater than or equal to 0.

As examples of strong protonic acids capable of being used in the process of the invention, mention may especially be made of sulfuric acid, aliphatic or aromatic sulfonic acids such as, for example, methanesulfonic acid, ethanesulfonic acid, benzenesulfonic acid, toluenesulfonic acids and naphthalenesulfonic acids.

Another class of strong protonic acids are the hydroxybenzenesulfonic acids, sulfonated hydroxybenzoic acids; hydroxybenzenedisulfonic acids, dihydroxybenzenedisulfonic acids, hydroxytoluenesulfonic acids, hydroxynaphthalenesulfonic acids and hydroxy-naphthalenedisulfonic acids and mixtures thereof.

Among the hydroxybenzenesulfonic acids, use will preferably be made of 4-hydroxybenzenesulfonic acid, 2-hydroxybenzenesulfonic acid, 5-sulfosalicylic acid or a mixture thereof.

The preferred dihydroxybenzenedisulfonic acids are 5,6-dihydroxy-1,3-benzenedisulfonic acid, 4,6-dihydroxy-1,3-benzenedisulfonic acid and 2,5-dihydroxy-1,4-benzenedisulfonic acid.

As other examples of acids, mention may especially be made of perhaloacetic acids such as trichloroacetic acid and trifluoroacetic acid.

As regards the second component of the mixture of acids, this is a superacid, that is to say an acid having a $pK_a$ (S) below that of sulfuric acid and which therefore has a negative $\Delta pK_a$.

The lower limit is not critical but generally the $\Delta pK_a$ in nitrobenzene is greater than or equal to −12.

The superacids preferably chosen in the process of the invention have a $\Delta pK_a$ less than or equal to −0.1 and preferably greater than or equal to −8.

Among the superacids that are suitable for the process of the invention, mention may more particularly be made of perchloric acid, halosulfonic acids such as fluorosulfonic acid or chlorosulfonic acid; perhaloalkanesulfonic acids, preferably trifluoromethanesulfonic acid.

Also as superacids, mention may be made, inter alia, of trifluoromethanesulfinic acid; or bis(trifluoromethane-sulfonyl)imide acid.

In accordance with the process of the invention, a mixed catalysis is required, that is to say two acids are used.

It would not be outside the scope of the invention to add an additional acid. Thus, the invention includes the case where a mixture of strong protonic acids or a mixture of superacids may be used.

As pairs of acids that are preferably chosen, mention may be made of perchloric acid and sulfuric acid; perchloric acid and 4-hydroxybenzenesulfonic acid; trifluoromethanesulfonic acid and 4-hydroxybenzenesulfonic acid; bis(trifluoromethanesulfonyl)-imide acid and 4-hydroxybenzenesulfonic acid.

The use of a mixed catalysis as mentioned above compared with a simple catalysis using a single strong protonic acid makes it possible to increase the amount of pyrocatechol formed with respect to the amount of hydroquinone.

The process of the invention makes it possible to obtain pyrocatechol/hydroquinone ratios that may advantageously vary between 1.4 and 2.2.

The proportion of the various acids may vary greatly.

Thus, use may be made of mixtures comprising:
from 60 mol % to 95 mol % of a strong protonic acid; and
from 5 mol % to 40 mol % of a superacid.
The mixtures preferably used comprise:
from 80 mol % to 95 mol % of a strong protonic acid; and
from 5 mol % to 20 mol % of a superacid.

Each percentage of acid expresses the ratio (expressed in %) between the number of moles of the acid in question and the number of moles of the sum of the two acids (strong protonic acid+superacid).

Compared to a mixture of defined acids, the variation of the relative proportion of each acid makes it possible to vary the pyrocatechol/hydroquinone ratio obtained.

Thus, the process of the invention makes it possible to obtain an adjustable ratio that thus makes it possible to adapt production to the market demand.

The acids used in the mixture are commercially available in solid form, liquid form or in the form of an aqueous solution, the concentration of which may vary between 5 and 95% by weight, preferably between 50 and 70% by weight.

The amount of strong protonic acid used expressed by the ratio between the number of moles of said acid and the number of moles of substrate advantageously varies between 0.01% and 0.1%. Thus, said molar ratio is preferably chosen between 0.015% and 0.06%.

The amount of superacid used expressed by the ratio between the number of moles of said acid and the number of moles of substrate advantageously varies between 0.002% and 0.05%. Thus, said molar ratio is preferably chosen between 0.003% and 0.03%.

In accordance with the process of the invention, a phenol or a phenol ether is reacted with hydrogen peroxide in the presence of the mixture of acids as defined.

The hydrogen peroxide employed according to the invention can be in the form of an aqueous solution or of an organic solution.

As aqueous solutions are more readily available commercially, they are preferably used.

The concentration of the aqueous hydrogen peroxide solution, although not critical per se, is chosen so as to introduce the least possible amount of water into the reaction medium. Use is generally made of an aqueous hydrogen peroxide solution comprising at least 20% by weight of $H_2O_2$ and preferably approximately 70%.

The amount of hydrogen peroxide may range up to 1 mol of $H_2O_2$ per 1 mol of substrate of formula (I).

However it is preferable, in order to obtain an industrially acceptable yield, to use a hydrogen peroxide/substrate of formula (I) molar ratio from 0.01 to 0.3 and, preferably, from 0.03 to 0.10.

As the amount of water influences the speed of the reaction, it is preferable to minimize its presence, it being possible for the water to be introduced into the reaction medium in particular via the reactants employed.

It is advisable to preferably choose an initial water content of the medium of less than 20% by weight and preferably of less than 10% by weight.

The water contents by weight indicated are expressed with respect to the substrate of formula (I)/hydrogen peroxide/water mixture.

This initial water corresponds to the water introduced with the reactants and in particular with the hydrogen peroxide.

An alternative form of the process of the invention consists in adding an agent which complexes the metal ions present in the medium as the latter are harmful to the satisfactory progression of the process of the invention, in particular in the case of phenols where the yields of hydroxylation products are low. Consequently, it is preferable to inhibit the action of the metal ions.

The metal ions harmful to the progression of the hydroxylation are ions of transition metals and more particularly iron, copper, chromium, cobalt, manganese and vanadium ions.

The metal ions are introduced by the reactants and in particular the starting substrates and the equipment used. In order to inhibit the action of these metal ions, it is sufficient to carry out the reaction in the presence of one or more complexing agents which are stable with regard to hydrogen peroxide and which give complexes which cannot be decomposed by the strong acids present and in which the metal can no longer exert chemical activity.

Recourse may in particular be had, as nonlimiting examples of complexing agents, to the various phosphoric acids, such as, for example, orthophosphoric acid, metaphosphoric acid, pyrophosphoric acid or polyphosphoric acids or phosphonic acids, such as (1-hydroxyethylidene)diphosphonic acid, phosphonic acid, ethylphosphonic acid or phenylphosphonic acid.

It is also possible to employ the esters of the abovementioned acids and mention may more particularly be made of monoalkyl or dialkyl, monocycloalkyl or dicycloalkyl or monoalkylaryl or dialkylaryl orthophosphates, for example ethyl or diethyl phosphate, hexyl phosphate, cyclohexyl phosphate or benzyl phosphate.

The amount of complexing agent depends on the content of metal ions in the reaction medium.

There is obviously no upper limit, it being possible for the amount of complexing agents present to be far in excess with respect to that necessary to complex the metal ions. Generally, an amount representing from 0.01% to 1% by weight of the reaction medium is highly suitable.

In accordance with the process of the invention, the hydroxylation of the substrate of formula (I) is carried out at a temperature which can be between 45° C. and 140° C.

A preferred alternative form of the process of the invention consists in choosing a temperature between 60° C. and 120° C.

The reaction is advantageously carried out at atmospheric pressure.

Pressures that are slightly higher or lower may also be used.

The process of the invention may also be carried out under an inert atmosphere, for example under nitrogen or else under argon, nitrogen being preferred in particular considering its lower cost.

The hydroxylation process is generally carried out without solvent other than that which originates from the reactants, such as the solvent of the hydrogen peroxide.

However, the reaction can also be carried out in an organic solvent.

The solvents used must be stable in the presence of hydrogen peroxide.

Mention may be made of nonpolar solvents, such as chlorinated aliphatic hydrocarbons, for example dichloromethane, tetrachloromethane or dichloroethane.

It is possible to use, in particular in the case of the hydroxylation of phenol ethers, more polar solvents, especially ethers, for example sulfolane or 1,2-dimethoxyethane but also acetonitrile or dimethylcarbonate.

From a practical viewpoint, the process according to the invention is simple to carry out continuously or batchwise.

The mixed catalyst of the invention can be employed in the substrate of formula (I) or in the hydrogen peroxide solution.

Preferably, the order of the following reactants is chosen: the substrate of formula (I), optionally the complexing agent and the mixture of strong acids are introduced.

The reaction medium is brought to the desired temperature and then the solution of hydrogen peroxide is added, gradually, in fractions or continuously.

According to a continuous embodiment, it is possible to carry out the process of the invention in one or more reactors in cascade.

Introduced into the first reactor are the substrate of formula (I), with optionally the complexing agent, the hydrogen peroxide solution; it being possible for the mixture of acids to be introduced alone or employed in the other reactants.

At the end of the reaction, the unconverted substrate and, if appropriate, the excess acids are separated from the hydroxylation products by the usual means, in particular by distillation and/or liquid/liquid extraction, and are returned to the reaction region.

In the examples, various acids are used, the acid strength of which is assessed in comparison with sulfuric acid, which is chosen as a reference.

The $\Delta pK_a$ of the acid in question with respect to sulfuric acid is determined in nitrobenzene by comparative potentiometric assaying.

The measurement protocol is the following:

Each of the acids (strong protonic acid or superacid and sulfuric acid) are dissolved in an amount of 0.2 mmol in 50 ml of nitrobenzene and 1 ml of isopropanol.

A tetrabutylammonium hydroxide solution (0.1N solution in isopropanol) is gradually added.

The potentiometric titration curve (pH as a function of volume of tetrabutylammonium hydroxide solution) is recorded at 20° C. using electrodes: either a combined pH electrode (suitable for the organic medium) or a glass electrode combined with an Ag/AgCl reference electrode filled with LiCl in an amount of 3 mol/l in methanol.

The results (expressed in mV±0.2) are given in $\Delta pK_a$ with respect to sulfuric acid (1st acidity), it being known that one unit of $pK_a$ is equal to 60 mV.

Some examples of results obtained are given:

trifluoromethanesulfonic (triflic) acid: $\Delta pK_{a\ (nitrobenzene)} = -1.0$ $HClO_4$: $\Delta pK_{a\ (nitrobenzene)} = -0.5$ TFSiH: $\Delta pK_{a\ (nitrobenzene)} = -0.1$ p-phenolsulfonic acid: $\Delta pK_{a\ (nitrobenzene)} = 0.1$ The examples which follow illustrate the invention without, however, limiting it.

In the examples, the following abbreviations signify:

The degree of conversion ($DC_{H2O2}$) of the hydrogen peroxide corresponds to the ratio of the number of moles of hydrogen peroxide converted to the number of moles of hydrogen peroxide introduced.

The yield of diphenols ($Y_{diphenols}$) corresponds to the ratio of the number of moles of diphenols formed (pyrocatechol+hydroquinone) to the number of moles of hydrogen peroxide introduced.

The pyrocatechol yield ($Y_{pyrocatechol}$) corresponds to the ratio of the number of moles of pyrocatechol formed to the number of moles of hydrogen peroxide introduced.

The hydroquinone yield ($Y_{hydroquinone}$) corresponds to the ratio of the number of moles of hydroquinone formed to the number of moles of hydrogen peroxide introduced.

The selectivity for diphenols ($S_{diphenols}$) corresponds to the ratio of the number of moles of diphenols formed (pyrocatechol+hydroquinone) to the number of moles of hydrogen peroxide converted.

The PC/HQ ratio is defined by the ratio of the number of moles of pyrocatechol to the number of moles of hydroquinone.

EXAMPLES

The procedure which will be followed in examples 1 to 4 is given below.

The following are charged at 50° C. to a 250 ml jacketed glass reactor equipped with a stirring system of 4 inclined blades type, with a vertical reflux condenser, with a nitrogen inlet and with a heating device:

117.6 g (1.25 mol) of phenol, pyrophosphoric acid in an amount of 0.03% of the weight of the phenol, a superacid, which is perchloric acid at 65% by weight or triflic acid, the amounts of which that are introduced are mentioned in the summarizing table (I), a strong protonic acid, which is either sulfuric acid at 98% by weight or 4-hydroxybenzenesulfonic acid (APS) at 65% by weight, the amounts of which that are introduced are mentioned in the summarizing table (I).

The various reactants used comprise less than 1 ppm of metals, especially iron.

The mixture is brought to a temperature of T° C. indicated in table (I), under a nitrogen atmosphere and then 3.03 g of 70 wt % aqueous hydrogen peroxide solution (i.e. 0.0625 mol of hydrogen peroxide) are added over 15 min using a syringe driver.

An increase in temperature accompanied by a coloring of the reaction mixture are generally observed.

Subsequently, the mixture is heated for 1 hour at the indicated temperature.

At the end of the reaction, the reaction mixture is cooled to 50° C. and the diphenols formed are quantitatively determined by high performance liquid chromatography.

Examples 1 to 3

The conditions and results obtained are recorded in table (I).

TABLE I

| | Example reference | | |
|---|---|---|---|
| | 1 | 2 | 3 |
| Catalyst | $HClO_4/H_2SO_4$ | $HClO_4/H_2SO_4$ | $CF_3SO_3H/APS$ |
| T (° C.) | 70° C. (15 min) then 70° C. (1 h) | 80° C. (15 min) then 90° C. (1 h) | 80° C. (15 min) then 80° C. (1 h) |
| $HClO_4$ mol %/PhOH | 0.0108% | 0.0080% | — |
| $CF_3SO_3H$ mol %/PhOH | — | — | 0.0042% |
| $H_2SO_4$ mol %/PhOH | 0.0597% | 0.0280% | — |
| APS mol %/PhOH | — | — | 0.0278% |
| DC ($H_2O_2$) | 100% | 100% | 100% |
| S (HQ)/$H_2O_2$ | 29% | 32% | 25% |
| S (PC)/$H_2O_2$ | 51% | 51% | 47% |
| S (HQ + PC)/$H_2O_2$ | 80% | 83% | 72% |
| PC/HQ ratio | 1.72 | 1.58 | 1.93 |

Comparative Examples A and B

In these comparative examples, it is demonstrated that the use of a perchloric acid/pyrophosphoric acid pair does not make it possible to act on the selectivity of the reaction.

The procedure given at the start of the examples is reproduced except that a strong protonic acid within the meaning of the invention is not used.

Use is made of only perchloric acid in example A and of a mixture of perchloric acid and pyrophosphoric acid in example B.

The conditions and results obtained are recorded in table (II).

TABLE II

| Example reference | A | B |
|---|---|---|
| Catalyst | Perchloric acid | Perchloric acid |
| Complexing agent | | Pyrophosphoric acid |
| T (° C.) | 80° C. (15 min) then 90° C. (1 h) | 80° C. (15 min) then 90° C. (1 h) |
| $HClO_4$ mol %/PhOH | 0.0330% | 0.0330% |
| DC ($H_2O_2$) | 100% | 100% |
| S (HQ)/$H_2O_2$ | 35% | 34% |
| S (PC)/$H_2O_2$ | 48% | 49% |
| S (HQ + PC)/$H_2O_2$ | 83% | 83% |
| PC/HQ ratio | 1.4 | 1.43 |

It emerges from the examination of this table that the use of a mixture of perchloric acid and pyrophosphoric acid has no influence on the selectivity of the reaction since the PC/HQ ratio is substantially identical.

Example 4

The procedure is reproduced but using a mixture of bis(trifluoromethanesulfonyl)imide acid (TFSiH) and APS.

The conditions and results obtained are recorded in the table below:

TABLE III

| Example reference | 4 |
|---|---|
| Catalyst | TFSiH/APS |
| T (° C.) | 80° C. (15 min) then 80° C. (3 h 30 min) |
| TFSiH mol %/PhOH | 0.0054% |
| APS mol %/PhOH | 0.0154% |
| DC ($H_2O_2$) | 100% |
| S (HQ)/$H_2O_2$ | 28% |
| S (PC)/$H_2O_2$ | 46% |
| S (HQ + PC)/$H_2O_2$ | 74% |
| PC/HQ ratio | 1.65 |

Example 5

The phenol (with the complexing agent), the hydrogen peroxide and the catalyst are introduced, in parallel and continuously, into a cascade of three 500 ml glass reactors.

Each jacketed reactor is equipped with a mechanical stirring system of 4 inclined blades type, with a system for regulating the temperature, with a vertical reflux condenser and with a nitrogen inlet.

534 g/h (5.68 mol) of phenol, 15.7 g/h of a 70 wt % aqueous hydrogen peroxide solution (i.e. 0.32 mol/h) and the mixture of perchloric and 4-hydroxybenzenesulfonic acids [0.18 g/h, i.e. 0.0203 mol % with respect to the phenol and 0.54 g/h, i.e. 0.0353 mol % with respect to the phenol respectively] are charged using pumps.

The temperature profile is as follows: 75° C. for the $1^{st}$ reactor, 86° C. for the second and 104° C. for the third.

After a stabilization time (approximately 1 h), the diphenols formed are quantitatively determined by high performance liquid chromatography and the hydrogen peroxide is quantitatively determined by potentiometry.

The operating conditions and results obtained in the $3^{rd}$ reactor are recorded in table (IV).

TABLE IV

| Example reference | 5 |
|---|---|
| APS catalyst mol %/PhOH | 0.0353% |
| $HClO_4$ catalyst mol %/PhOH | 0.0203% |
| DC $H_2O_2$ | 91% |
| Y HQ | 26% |
| Y PC | 45% |
| PC/HQ ratio | 1.72 |
| S (PC + HQ)/$H_2O_2$ | 78% |

The invention claimed is:
1. A process for the hydroxylation of a substrate, wherein the process comprises reacting said substrate with hydrogen peroxide, in the presence of an effective amount of an acid catalyst and obtaining pyrocatechol (PC) and hydroquinone (HQ) at a ratio of PC/HQ of between 1.4 and 2.2, wherein the substrate is a phenol, a phenol ether, or a substituted phenolic compound, and wherein the substrate has at least one hydrogen atom at the ortho and para position of the hydroxyl or ether group, and wherein the acid catalyst comprises a mixture of at least two strong acids one of the strong acids is a strong protonic acid having a $pk_a$ (S) greater than or equal to that of sulfuric acid and a $\Delta pK_a$ (S) with respect to sulfuric acid of less than or equal to 4 and greater than or equal to 0, and wherein the strong protonic acid does not include an oxyacid of phosphorus in the +5 oxidation state, and the other acid being selected from superacids.

2. The process as claimed in claim 1, wherein the strong protonic acid has a $\Delta pK_a$ (S) with respect to sulfuric acid of less than or equal to 3 and greater than or equal to 0.

3. The process as claimed in claim 1, wherein the strong protonic acid is selected from the group consisting of sulfuric acid, aliphatic or aromatic sulfonic acids, perhaloacetic acids, and mixtures thereof.

4. The process as claimed in claim 3, wherein the strong protonic acid is selected from the group consisting of sulfuric acid, 4-hydroxybenzenesulfonic acid, 2-hydroxybenzenesulfonic acid, 5-sulfosalicylic acid, 5,6-dihydroxy-1,3-benzenedisulfonic acid, 4,6-dihydroxy-1,3-benzenedisulfonic acid, and 2,5-dihydroxy-1,4-benzenedisulfonic acid.

5. The process as claimed in claim 1, wherein the superacid has a $pk_a$(S) below that of sulfuric acid.

6. The process as claimed in claim 5, wherein the superacid has a $\Delta pK_a$ relative to sulfuric acid of greater than or equal to −12.

7. The process as claimed in claim 5, wherein the superacid has a $\Delta pK_a$ relative to sulfuric acid of less than or equal to −0.1.

8. The process as claimed in claim 5, wherein the superacid is selected from the group consisting of perchloric acid, halosulfonic acids, perhaloalkanesulfonic acids, and mixtures thereof.

9. The process as claimed in claim 1, wherein the mixture of strong acids comprises perchloric acid and sulfuric acid; perchloric acid and 4-hydroxybenzenesulfonic acid; trifluoromethanesulfonic acid and 4-hydroxybenzenesulfonic acid; or bis(trifluoromethanesulfonyl)imide acid and 4-hydroxybenzenesulfonic acid.

10. The process as claimed in claim 1, wherein the mixture comprises:

from 60 mol % to 95 mol %, of a strong protonic acid; and from 5 mol % to 40 mol %, of a superacid.

11. The process as claimed in claim 1, wherein the amount of strong protonic acid used expressed by the ratio between the number of moles of said acid and the number of moles of substrate varies between 0.01% and 0.1%.

12. The process as claimed in claim 1, wherein the amount of superacid used expressed by the ratio between the number of moles of said acid and the number of moles of substrate varies between 0.002% and 0.05%.

13. The process as claimed in claim 1, wherein the substrate is a compound of formula (I):

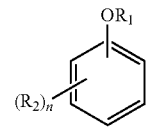

wherein:

n is a number from 0 to 4;

$R_1$ represents a hydrogen atom, or an alkyl, cycloalkyl, aryl or aralkyl group; and $R_2$, which are identical or different, represent an alkyl group, an alkoxy group, a hydroxyl group, a halogen atom, a haloalkyl or perhaloalkyl group.

14. The process as claimed in claim 13, wherein the substrate is selected from the group consisting of phenol; aliphatic ethers of phenols; monoalkylphenols, dialkylphenols, trialkylphenols with $C_1$-$C_4$ alkyl groups; and alkoxyphenols with $C_1$-$C_4$ alkoxy groups.

15. The process as claimed in claim 13, wherein the substrate is selected from the group consisting of phenol, anisole, phenetole; o-cresol, m-cresol; 2-methoxyphenol (guaiacol), and 2-ethoxyphenol (guaethol).

16. The process as claimed in claim 13, wherein the hydrogen peroxide/substrate of formula (I) molar ratio varies from 0.01 to 0.3.

17. The process as claimed in claim 1, wherein the process is carried out in the presence of an agent for complexing transition metal ions, which is stable under the reaction conditions, selected from the group consisting of phosphoric acids, polyphosphoric acids, phosphonic acids, and their ester acids.

18. The process as claimed in claim 1, wherein the process is carried out at a temperature between 45° C. and 140° C.

19. The process as claimed in claim 13, wherein the process comprises introducing a substrate of formula (I), optionally the complexing agent and the mixture of strong acids into an reaction medium, bringing the reaction medium to a desired temperature, and then adding hydrogen peroxide gradually, in fractions or continuously to the reaction medium.

20. The process as claimed in claim 1, wherein the process is carried out in batch mode or in continuous mode.

21. The process as claimed in claim 3, wherein when the strong protonic acid is an aliphatic acid or aromatic sulfonic acid, the strong protonic acid is selected from the group consisting of methanesulfonic acid, ethanesulfonic acid, benzenesulfonic acid, toluenesulfonic acid, naphthalenesulfonic acid; hydroxybenzenesulfonic acid, sulfonated hydroxybenzoic acid, hydroxybenzenedisulfonic acid, dihydroxybenzenedisulfonic acid, hydroxytoluenesulfonic acid, hydroxynaphthalenesulfonic acid, and hydroxynaphthalenedisulfonic acid.

22. The process as claimed in claim 3, wherein when the strong protonic acid is a perhaloacetic acid, the strong protonic acid is a trichloroacetic acid or trifluoroacetic acid.

23. The process as claimed in claim 7, wherein the superacid has a $\Delta pK_a$ relative to sulfuric acid of less than or equal to −0.1 and greater than or equal to −8.

24. The process as claimed in claim 8, wherein when the superacid is a halosulfonic acid, the super acid is fluorosulfonic acid or chlorosulfonic acid.

25. The process as claimed in claim 8, wherein when the superacid is a perhaloalkanesulfonic acid, the superacid is trifluoromethanesulfonic acid or bis(trifluoromethanesulfonyl)imide acid.

26. The process as claimed in claim 10, wherein the mixture comprises 80 mol % to 95 mol % of a strong protonic acid and from 5 mol % to 20 mol % of a superacid.

27. The process as claimed in claim 11, wherein the amount of strong protonic acid used expressed by the ratio between the number of moles of said acid and the number of moles of substrate varies between 0.015% and 0.06%.

28. The process as claimed in claim 12, wherein the amount of superacid used expressed by the ratio between the number of moles of said acid and the number of moles of substrate varies between 0.003% and 0.03%.

29. The process as claimed in claim 16, wherein the hydrogen peroxide/substrate of formula (I) molar ratio varies from 0.03 to 0.10.

30. The process as claimed in claim 17, wherein the phosphoric acid is selected from the group consisting of orthophosphoric acid, metaphosphoric acid, and pyrophosphoric acid.

31. The process as claimed in claim 17, wherein the phosphonic acid is selected from the group consisting of (1-hydroxyethylidene)diphosphonic acid, phosphonic acid, ethylphosphonic acid, and phenylphosphonic acid.

32. The process as claimed in claim 18, wherein the process is carried out at a temperature between 60° C. and 120° C.

33. The process of claim 13, wherein n in formula (I) is 0, 1, or 2.

\* \* \* \* \*